United States Patent [19]

Roman

[11] 4,241,081
[45] Dec. 23, 1980

[54] CYCLOPROPANECARBOXYLATE PESTICIDES

[75] Inventor: Steven A. Roman, Oakdale, Calif.

[73] Assignee: Shell Oil Company, Houston, Tex.

[21] Appl. No.: 59,854

[22] Filed: Jul. 23, 1979

Related U.S. Application Data

[63] Continuation-in-part of Ser. No. 953,987, Oct. 23, 1978, abandoned.

[51] Int. Cl.$^3$ .................... A01N 53/00; C07C 69/757; C07C 121/75
[52] U.S. Cl. ............................... 424/304; 260/465 D; 424/305; 424/308; 560/73; 560/124; 560/231; 562/506; 568/591; 568/303; 568/367; 568/420
[58] Field of Search ............ 260/465 D, 326 A, 347.4; 560/60, 73, 118, 124; 424/304, 305, 308

[56] References Cited

U.S. PATENT DOCUMENTS

| | | | |
|---|---|---|---|
| 3,687,172 | 7/1972 | Hill et al. ........................ | 424/306 |
| 3,708,528 | 1/1973 | Mukheyee et al. ............... | 562/506 |

FOREIGN PATENT DOCUMENTS 862461  6/1978  Belgium.
2639777  3/1977  Fed. Rep. of Germany.

OTHER PUBLICATIONS

Sevrin et al., Tetrahedron Letters, No. 43, pp. 3915-3918 (1976).
Cocker et al., J. Chem. Soc. Perkins Trans. I, pp. 332-335 (1975).

*Primary Examiner*—Dolph H. Torrence

[57] ABSTRACT

Compounds of the formula

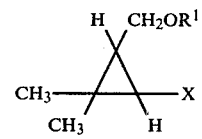

wherein $R^1$ is an acyl group or certain optionally halosubstituted hydrocarbyl groups, and X is —CH$_2$CH(OCH$_3$)$_2$, —CH$_2$CHO, —CH=CHOR$^2$ in which R$^2$ is acyl,—CHO,—C(O)Cl, —C(O)Br or —C(O)OR in which R is H, a salt-forming cation, an alkyl group or the residue of a pyrethroid alcohol are new pesticides or intermediates therefore. The compounds are prepared using a multi-step synthesis starting from the natural terpene, 3-carene.

8 Claims, No Drawings

CYCLOPROPANECARBOXYLATE PESTICIDES

This application is a continuation-in-part of application Ser. No. 953,987, filed on Oct. 23, 1978 now abandoned.

FIELD OF THE INVENTION

The present invention is directed to new cyclopropanecarboxylate pesticides, their use in pest control, to pest control formulations containing the new cyclopropanecarboxylates, to processes for preparation of these cyclopropanecarboxylates and to novel intermediates.

SUMMARY OF THE INVENTION

The present invention relates to new cyclopropane compounds of the formula

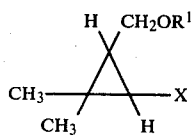

wherein $R^1$ represents an acyl group containing from 1 to 10 carbon atoms; an alkyl group containing from 1 to 10 carbon atoms optionally substituted by one or more halogen atoms; a (cycloalkyl)alkyl group containing from 3 to 7 ring carbon atoms, a total of from 4 to 9 carbon atoms and optionally ring-substituted by one or more halogen atoms; a cycloalkyl group containing from 3 to 7 ring carbon atoms; an alkenyl group containing from 2 to 4 carbon atoms optionally substituted by one or more halogen atoms; an alkynyl group containing from 2 to 4 carbon atoms or an aryl group containing from 6 to 12 carbon atoms or an aralkyl group containing from 7 to 10 carbon atoms, each optionally ring-substituted by one or more halogen atoms;

X is $-CH_2CH(OCH_3)_2$, $-CH_2CHO$, $-CH=CHOR^2$ in which $R^2$ is an acyl group containing from 1 to 5 carbon atoms, $-CHO$, $-C(O)Cl$, $-C(O)Br$, or $-C(O)OR$ in which R represents a hydrogen atom, a salt-forming cation, an alkyl group containing from 1 to 20 carbon atoms or a group of the formula

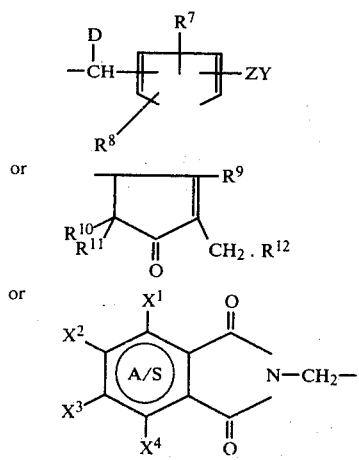

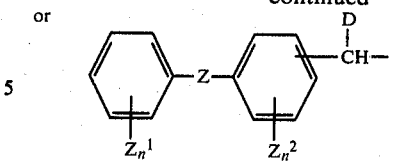

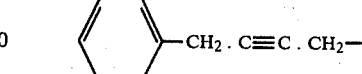

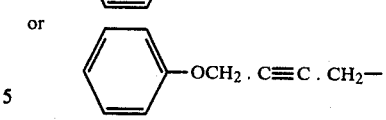

wherein Y represents hydrogen or an alkyl, alkenyl or alkynyl group or an aryl or furyl group which is unsubstituted or substituted in the ring by one or more alkyl, alkenyl, alkoxy or halogeno groups, $R^7$ and $R^8$, which may be the same or different, each represents hydrogen or an alkyl or alkenyl group. $R^9$ represents hydrogen or a methyl group, $R^{10}$ and $R^{11}$ represent hydrogen or an alkyl group, $R^{12}$ represents an organic radical having carbon-carbon unsaturation in a position $\alpha$ to the $CH_2$ group to which $R_{12}$ is attached, A/S indicates an aromatic ring or a dihydro or tetrahydro analog thereof, $X^1$, $X^2$, $X^3$ and $X^4$, which may be the same or different, each represent hydrogen, halogen or a methyl group, D represents H, $-CN$, $-C\equiv CH$ or

in which $R^{13}$ and $R^{14}$ may be the same or different, each represent a hydrogen atom or an alkyl group containing from 1 to 10 carbon atoms, Z represents $-CH_2-$, $-O-$, $-CO-$, or $-S-$, $Z^1$ and $Z^2$, which may be the same or different, each represent halogen or an alkyl group containing 1 to 4 carbon atoms and n is 0, 1 or 2, with the proviso that when D is $-CN$, $-C\equiv CH$ or

then the alcohol moiety is in the R,S-racemic or in the S-optical configuration.

The above esters of the present invention wherein X is C(O)OR in which R is a group of formula I, II, III, IV, V or VI are useful pest control agents.

The other cyclopropane compounds described above are useful intermediates for the production of the pest control esters.

When the (1R, cis) ester is one formally derivable from a furylmethyl alcohol, it is preferred that the furyl methyl alcohol be a 3-furylmethyl alcohol as described and claimed in U.S. Pat. No. 3,466,304.

In the furylmethyl alcohols (R is formula I), and particularly in the 3-furyl-methyl alcohols, it is preferred that $R^7$ and $R^8$ each represent hydrogen or groups containing up to 4 carbon atoms, particularly a methyl group and that Y represents a phenyl group which is unsubstituted or substituted in the ring by a group containing up to 4 carbon atoms, e.g., methyl or methoxy, or by chlorine and Z is $CH_2$ and D is H. Analogues of these compounds where Z is O, S or CO and D is —CN or —C≡CH are also of interest. Further compounds of interest are those where Y represents a hydrogen atom, an alkyl group containing up to 4 carbon atoms, an alkenyl group containing up to 4 carbon atoms, e.g., vinyl, an alkadienyl group containing up to 4 carbon atoms or an alkynyl group, e.g., propargyl, or a furyl group.

Specific alcohols of this category, from which the (1R,cis) esters of the invention are formally derivable, includes 5-benzyl-3-furylmethyl alcohol, 5-benzyl-2-methyl-3-furylmethyl alcohol, 5-benzyl-3-furylmethyl alcohol, 4-benzyl-5-methyl-2-furylmethyl alcohol, 5-(p-methylbenzyl)methyl-3-furylmethyl alcohol, 2,4,5-trimethyl-3-furylmethyl alcohol and 4,5-dimethyl-2-furylmethyl alcohol, 5-phenoxy-and 5-benzoyl-3-furylmethyl alcohol and α-cyano substituted 4-benzyl-, 5-benzyol- or 5-phenoxy-3-furylmethyl alcohol.

The cyclopentenolones from which the (1R,cis) esters of the invention are formally derivable are those unsubstituted in the 3-position or those substituted in the 3-position by a methyl group ($R^9$=H or $CH_3$).

The cyclopentenolones (R is formula II) unsubstituted in the 2-position are described and claimed in U.S. Pat. No. 3,720,703.

Some of these alcohols are the 3-desmethyl analogues of the alcohols from which the naturally occurring pyrethrins are derived. In the present invention, it is preferred that $R^{10}$ and $R^{11}$ each represent hydrogen, methyl or ethyl and $R^{12}$ represents an aryl group such as a phenyl group or a phenyl group substituted by a halogeno or alkyl or alkoxy substituent of 1 to 4 carbon atoms, for example, tolyl, xylyl, p-chlorophenyl or p-methoxyphenyl. $R^{12}$ may also represent a 2- or 3-furyl group or an alkenyl group such as vinyl, 1-propenyl or 1,3-butadienyl group.

When the (1R,cis) esters of the invention are formally derivable from the cyclopentenolones which are substituted in the 3-position by the methyl group ($R^9$=methyl), the (1R,cis) esters may be derived from allethrolone ($R^{10}=R^{11}$=H, $R^{12}$=vinyl), pyrethrolone ($R^{10}=R^{11}$=H, $R^{12}$=1,3-butadienyl), cinerolone ($R^{10}=R^{11}$=H, $R^{12}$=1-propenyl, jasmolone ($R^{10}=R^{11}$=H, $R^{12}$=1-butenyl), or furethrolone ($R^{10}=R^{11}$=H, $R^{12}$=2-furyl).

When the (1R,cis) esters of the invention are phthalimidomethyl esters where R is of formula III, they may be phthalimido, dihydrophthalimido or tetrahydrophthalimidomethyl esters where the phthalimido, dihydrophthalimido or tetrahydrophthalimido residue (R is formula III) is one described in British Pat. Specifications Nos. 985,006, 1,052,119 or 1,058,309. 3,4,5,6-Tetrahydrophthalimidomethyl esters are of particular interest.

When the (1R,cis) esters of the invention are those where R is of formula IV, it is preferred that they be 3-benzylbenzyl esters, 3-benzoylbenzyl esters, or 3-phenoxybenzyl esters although each of the rings may be substituted by up to 3 chloro and/or methyl groups. Other esters of particular interest where R is of formula IV are those where Z represents O or $CH_2$ and D represents —CN or —C≡CH, e.g., esters of α-cyano or α-ethynyl substituted 3-phenoxy-, 3-benzyl or 3-benzyloxy benzyl alcohol. Such alcohols are described in U.S. Pat. Nos. 3,666,789, 3,835,176 and 3,862,174.

A preferred subclass of compounds of the invention are those wherein $R^1$ is an alkyl group containing from 1 to 6 carbon atoms; a (cycloalkyl)alkyl group containing from 3 to 6 carbon atoms and 4 to 8 carbon atoms in the group; a cycloalkyl group containing from 3 to 6 carbon atoms; an alkenyl or alkynyl group containing from 2 to 4 carbon atoms; an aryl group containing from 6 to 12 carbon atoms or an aralkyl group containing from 7 to 10 carbon atoms and X is —C(O)OR in which R is phenoxybenzyl or especially α-cyano-3-phenoxybenzyl. The compounds wherein $R^1$ is an alkyl of from 1 to 3 carbon atoms, especially ethyl, have been found to have insecticidal activity, e.g., against corn earworm larvae.

The cyclopropane compounds exhibit optical isomerism by virtue of two asymmetric centers in the cyclopropane ring and consequently can be prepared in optically active forms, which can subsequently be mixed together, or as racemic mixtures, which can subsequently be resolved into optically active forms. Because they usually provide the highest degree of pest control, the (1R,cis) esters are preferred although the (1R,trans) esters are also active. In the esters of α-substituted alcohols in which D in formulas I or IV is other than hydrogen, there is a further possibility of optical isomerism, i.e., as R or as S optical configuration. The esters in which these alcohols exist in the R optical configuration are without practical control activity.

The invention also relates to processes for preparing the new pest control cyclopropanecarboxylates described above from 3-carene. When (+)—Δ³-carene is used the pesticidal ester products have the (1R,cis) optional configuration.

Basically, the hydrocarbyloxymethyl-2,2-dimethylcyclopropanecarboxylic acids are prepared by a multistep process in which 3-carene having the formula VII

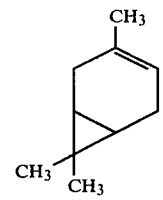

is ozonized and treated with dimethyl sulfide in methanol to form 1-(2,2-dimethoxyethyl)-2,2-dimethyl-3-(2-oxopropyl)cyclopropane, a novel chemical having the formula VIII,

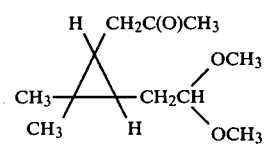

which is oxidized to (2-(2,2-dimethoxyethyl)-3,3-dimethylcyclopropyl)-methyl acetate having the formula IX

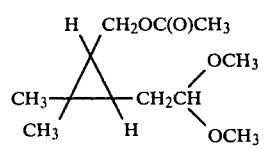

Hydrolysis of the above acetate derivative yields (2,2-dimethyl-3-(2,2-dimethyloxyethyl)cyclopropyl)methanol having the formula X.

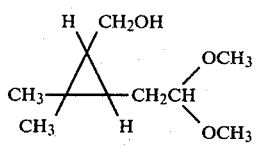

The above compound is converted to a compound having the formula XI

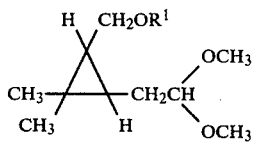

wherein $R^1$ is an optionally substituted hydrocarbyl group as described earlier. Hydrolysis of the above compound yields an aldehyde derivative having the formula XII,

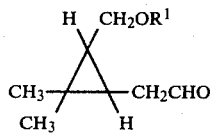

which reacts with a carboxylic acid anhydride, e.g., acetic anhydride, to produce a 2-(2,2-dimethyl-3-(hydrocarbyloxymethyl)cyclopropyl)vinyl ester having the formula XIII

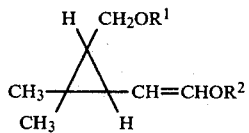

wherein $R^2$ is an acyl group containing from 1 to 5 carbon atoms. Ozonolysis of the above vinyl ester derivative and treatment with zinc forms a 2,2-dimethyl-3-(hydrocarbyloxymethyl)cyclopropanecarboxaldehyde having the formula XIV.

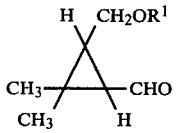

Oxidation of the above compound of formula XIV yields a 2,2-dimethyl-3-(hydrocarbyloxymethyl)cyclopropanecarboxylic acid, useful for the preparation of ester pest control agents of the invention wherein $R^1$ is an optionally substituted hydrocarbyl group as described above and X is —C(O)OR in which R is a group of formulas I—VI, inclusive.

The acetoxymethyl-2,2-dimethylcyclopropanecarboxylic acid is prepared by a multi-step process in which 3-carene is ozonized and treated with dimethyl sulfide in methanol to form 1-(2,2-dimethoxyethyl)-2,2-dimethyl-3-(2-oxopropyl)cyclopropane as described earlier. This product is oxidized to (2-(2,2-dimethoxyethyl)-3,3-dimethylcyclopropyl)-methyl acetate IX as described earlier. This acetate derivative is hydrolyzed in the presence of acid to (2,2-dimethyl-3-(2-oxoethyl)-cyclopropyl)methyl acetate having the formula XV

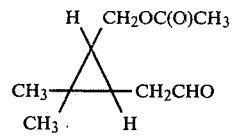

Treatment of the above compound with acetic anhydride in the presence of a base produces 2-(3-acetoxymethyl-2,2-dimethylcyclopropyl)vinyl acetate having the formula XVI

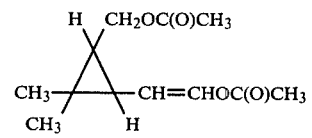

Ozonolysis and treatment with zinc of the above vinyl acetate derivative yields 3-acetoxymethyl-2,2-dimethylcyclopropanecarboxaldehyde having the formula XVII

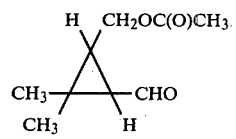

Oxidation of the above compound yields 3-acetoxymethyl-2,2-dimethylcyclopropanecarboxylic acid, useful for the preparation of ester pest control agents of the invention wherein $R^1$ is acetyl and X is —C(O)OR in which R is a group of the formulas I–VI, inclusive.

The ozonolysis reactions are conducted with a gaseous mixture comprising ozone and oxygen or ozone and air. The mixture of ozone and oxygen is suitably diluted with an inert gas, such as nitrogen or argon. The ozonolysis is carried out at a temperature from about $-80°$ C. to $+20°$ C., perferably from about $-20°$ C. to $+20°$ C. It is useful in certain cases to use a solvent. Suitable solvents include aromatic hydrocarbons such as benzene and toluene, halogenated hydrocarbons, such as methylene dichloride, chloroform, and the like, lower aliphatic carboxylic acids and esters thereof such as glacial acetic acid, ethyl acetate, and the like, aliphatic hydrocarbons, such as n-hexane and the like, and lower alkanols such as methanol.

Oxidation of the compound of formulas VIII, XIV and XVI is conducted using reagents which convert an aldehyde into an ester or acid group as required. For example, the compound of formula VIII is oxidized by hydrogen peroxide, or a peracid, such as m-chloroperbenzoic acid, perbenzoic acid, perphthalic acid, and the like, in a suitable solvent such as chlorinated hydrocarbon, e.g., chloroform or dichloroethylene, or an ether, e.g., diethyl ether, and the compounds of formulas XIV and XVII are oxidized using potassium permanganate, chromic acid, postassium dichromate or the like. Such oxidations are conveniently carried out in the liquid phase by agitating, e.g., stirring a mixture of the reactants, preferably in a solvent such as an acetone-water mixture. The reaction is conducted at a temperature of from about 0° C. to about 60° C. at normal pressures.

Preferably, the reactions are conducted at a temperature of from about 10° C. to about 40° C.

The acetate derivative of formula IX is converted into the cyclopropylmethanol derivative of formula X by hydrolysis, preferably under basic conditions, for example using an alkali or alkaline earth metal hydroxide or carbonate, such as sodium hydroxide, potassium hydroxide, sodium carbonate or the like, in an aqueous alcoholic reaction medium, such as aqueous methanol, ethanol or the like.

The hydroxy group of derivative of formula X is converted into an ether group by treatment with an optionally substituted hydrocarbyl halide, $R^1Hal$ in which $R^1$ is a group as previously defined and Hal is chlorine, bromine or iodine. Such treatment is suitably in the presence of an alkali metal hydride, such as sodium hydride or potassium hydride, preferably in the presence of an inert solvent, such as tetrahydrofuran, dimethylformamide, and the like, or in the presence of a hydrocarbyl lithium compound, such as an alkyl, aryl or aralkyl lithium compound, e.g., n-butyl lithium and the like, another preferably in the presence of an inert solvent, such as tetrahydrofuran, and the like.

The acetals IX and XI are converted into the aldehydes of formulas XV and XII, respectively, by treatment with an acidic material in an aqueous environment. Preferred acidic materials are acetic acid or hydrochloric acid used in the form of an aqueous solution thereof.

The compounds of formulas XV and XII are converted into ester derivatives of formulas XVI and XIII, respectively, by treatment with the appropriate carboxylic acid anhydride, e.g., acetic anhydride, in the presence of a basic material. Suitable basic materials include tertiary amines, and alkali acetates. Preferred amines are pyridine and especially triethylamine.

The acetate derivatives of formulas XVI and XIII are converted to the aldehydes of formulas XVI and XIV, respectively, by ozonolysis as previously described and by treatment with zinc in the presence of acetic acid or with a basic material, preferably triethylamine, usually in an inert solvent, such as methylene chloride or the like.

The alcohols from which the groups of formulas I through VI, inclusive, are known in the art, as for example in Elliott et al. U.S. Pat. No. 3,922,269 or Belgian patent 839,360. The pest control esters of the present invention can be prepared by esterification involving the reaction of an alcohol or derivative thereof of formula RQ, e.g., of formula IV, and a cyclopropanecarboxylic acid or derivative of formula XVIII

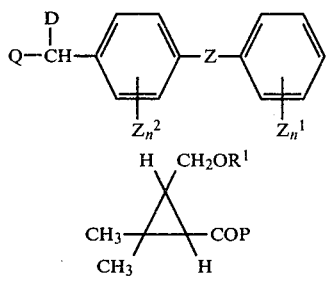

wherein Q and COP are functional groups or atoms which will react to form an ester linkage and $R^1$, D, Z, $Z^1$ and $Z^2$ are as defined above.

It is usually convenient in practice either to treat the acid or acid halide with the alcohol (COP=COOH or CO—halide and Q=OH) or to treat a halogeno compound (Q=halogen) with a salt of the carboxylic acid (COP=COO—M) where M is, for example, a silver or ammonium cation.

It can be useful to prepare the intermediate alkyl ester as tert-butyl ester (R=tert—butyl), which can be selectively converted under acid conditions as mentioned earlier to give the free acid which can be esterified, e.g., after conversion to the acid halide, to a pesticidal ester.

Suitable routes to the esters in which D is

are similar to those described in Belgian patent 839,360. One route involves treating the corresponding nitrile (D is —CN) with hydrogen sulfide in the presence of a basic catalyst, preferably in the presence of a solvent. Useful solvents are lower alkanols, pyridine, or preferably a dipolar aprotic solvent, such as dimethylformamide or hexamethylphosphoramide. The catalyst is preferably a strong nitrogeneous base, particularly a tertiary amine such as triethylamine, trimethylamine, or the like, or an alkanolamine, such as triethanolamine, and the like. The reaction can be carried out at room temperature. It is desirable that the reaction solution be saturated with hydrogen sulfide. Alcohols of formula RQ where R is a group of formula IV may be prepared by reduction of the corresponding acids, esters or aldehydes e.g., with hydride, or by conversion of the corresponding halide to an ester, e.g., by reaction with sodium acetate, followed by hydrolysis of the ester, or by reaction with formaldehyde of a Grignard reagent derived from the corresponding halide. The halides of formula RQ where R is a group of formula IV can be prepared by halomethylation of the compound

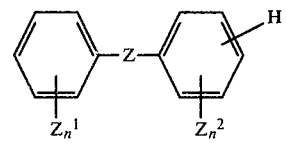

or side chain halogenation of

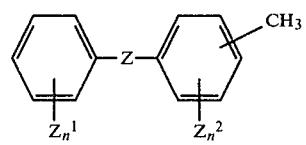

As stated earlier, the esters wherein $R^1$ is an acetyl or optionally substituted hydrocarbyl group are useful pest control agents having the ability to knockdown insects, such as houseflies, or repel mites and/or to kill insects or mites. The particular mode of pest control activity (high knockdown, repelling or killing action) can vary with the individual cyclopropanecarboxylate ester of the invention and thus depends on the specific combination of acid and alcohol moieties. In general, the pest control mode of action of the esters of the invention wherein $R^1$ is acetyl is knockdown or mite repelling rather than a killing action. In the esters wherein $R^1$ is optionally substituted hydrocarbyl, high knockdown is present and often mite repelling, insecticidal and acaricidal activity as well.

The invention includes, within its scope, pest control compositions comprising an agriculturally acceptable adjuvant—that is, at least one carrier or a surface-active agent—and, as active ingredient, at least one pest control ester of this invention. Likewise, the invention includes also a method of controlling insect, acarine or other arthropod pests at a locus which comprises applying to the pests or to the locus a pest controlling effective amount of at least one ester of the invention.

With respect to the spectrum of pesticidal activity, the compounds of this invention exhibit a selective or non-selective activity as insecticides or acaricides against one or more species of such orders as Coleoptera, Lepidoptera (especially larvae), Diptera, Orthoptera, Hemiptera, Homoptera and Acarina depending upon the specific combination of acid and alcohol moieties according to the present invention. The compositions according to the present invention are useful for controlling one or more disease carrying insects such as mosquitos, flies and cockroaches, grain insects such as rice weevil (*Sitophilus oryzae*) and mites as well as agricultural noxious insects such as planthoppers, green rice leafhopper (*Nephotettix bipuntatus cinticeps* Uhler), diamond-back moths (*Plutella maculipennis* Curtis), imported cabbage worm (*Pieris rapae* Linne), rice stem borers (*Chilo suppressalis* Walker), corn earworm larvae (*Haleiothis zea* Boddie), aphids, tortrixes, leaf-miners and the like.

The pesticidal esters of the invention are used for harvested crops, horticultural application, forests, cultures in green house, and packaging materials for foodstuffs.

The term "carrier" as used herein means a material that may be inorganic or organic and of synthetic or natural origin with which the active compound is mixed or formulated to facilitate its application to the plant, seed, soil and other object to be treated, or its storage, transport or handling. The carrier may be a solid or a liquid.

Suitable solid carriers may be natural and synthetic clays and silicates, for example, natural silicas such as diatomaceous earths; magnesium silicates, for example, talcs; magnesium aluminum silicates; for example, attapulgites and vermiculites; aluminum silicates, for example, kaolinites, montmorillonites and micas; calcium carbonate; calcium sulfate; synthetic hydrated silicon oxides and synthetic calcium or aluminum silicates; elements such as for example, carbon and sulfur; natural and synthetic resins such as, for example, coumarone resins, polyvinyl chloride and styrene polymers and copolymers; solid polychlorophenols; bitumen, waxes such as beeswax, paraffin wax, and chlorinated mineral waxes; degradable organic solids, such as ground corn cobs and walnut shells; and solid fertilizers, for example superphosphates.

Suitable liquid carriers include solvents for the compounds of this invention and liquids in which the toxicant is insoluble or only slightly soluble.

Examples of such solvents and liquid carriers, generally, are water, alcohols, for example, isopropyl alcohol, ketones, such as acetone, methyl ethyl ketone, methyl isobutyl ketone and cyclohexanone; ethers; aromatic hydrocarbons such as benzene, toluene and xylene; petroleum fractions, such as kerosene, light mineral oils, chlorinated hydrocarbons, such as methylene chloride, perchlorethylene, trichloroethane, including liquidfied normally vaporous gaseous compounds. Mixtures of different liquids are often suitable.

If used, the surface-active agent may be an emulsifying agent or a dispersing agent or a wetting agent. It may be nonionic, ionic or preferably, mixtures of both. Surface-active agents usually applied in formulating pesticides may be used. Examples of such surface-active agents are the sodium or calcium salts of polyacrylic acids and lignin sulfonic acids; the condensation products of fatty acids or aliphatic amines or amides containing at least 12 carbon atoms in the molecule with ethylene oxide and/or propylene oxide; fatty acid esters of glycerol, sorbitan, sucrose or pentaerythritol; fatty acids salts of low molecular weight, mono-, di-, and trialkyl-amines; condensates of these with ethylene oxide and/or propylene oxide; condensation products of fatty alcohols or alkyl phenols, for example, p-octylphenol or p-octylcresol, with ethylene oxide and/or propylene oxide; sulfates or sulfonates of these condensation products; alkali or alkaline earth metal salts, preferably sodium salts of sulfonated castor oil, and sodium alkylaryl sulfonates such as sodium dodecylbenzene sulfonate; and polymers of ethylene oxide and copolymers of ethylene oxide and propylene oxide.

The compositions of the invention may be formulated as wettable powders, dusts, granules, solutions, emulsifiable concentrates, emulsions, suspension concentrates or aerosols. Encapsulated formulations and controlled release formulations are also contemplated, as are bait formulations. Wettable powders are usually compounded to contain 25, 50 or 75% w of toxicant and usually contain, in addition to solid carrier, 3-10% w of stabilizer(s) and/or other additives such as penetrants or stickers. Dusts are usually formulated as a dust concentrate having a similar composition to that of a wettable powder but without a dispersant, and are diluted in the field with further solid carrier to give a composition usually containing ½-10% w of toxicant. Granules may be manufactured by extrusion of plastics, agglomeration or impregnation techniques. Generally, granules will contain ½-25% w toxicant and 0-10% w of additives such as stabilizers, slow release modifiers and binding agents. Emulsifiable concentrates usually contain, in addition to the solvent, and when necessary, cosolvent, 10-50% w/v toxicant, 2-20% w/v emulsifiers and 0-20% w/v of appropriate additives such as stabilizers, penetrants aand corrosion inhibitors. Suspension concentrates are compounded so as to obtain a stable, non-sedimenting, flowable product and usually contain 10-75% w toxicant, 0-5% w of dispersing agents, 0.1-10% w of suspending agents such as protective colloids and thixotropic agents 0-10% w of appropriate additives such as deformers, corrosion inhibitors, stabilizers, penetrants and stickers, and as carrier, water or an organic liquid in which the toxicant is substantially insoluble; certain organic additives or inorganic salts may be dissolved in the carrier to assist in preventing sedimentation or as antifreeze agents for water.

Aqueous dispersions and emulsions, for example, compositions obtained by diluting a wettable powder or an emulsifiable concentrate according to the invention with water, also lie within the scope of the present invention.

The compositions of the invention can also contain other ingredients, for example, other compounds possessing pesticidal, herbicidal or fungicidal properties, or attractants, such as pheromones, attractive food ingredients, and the like, for use in baits and trap formulations.

Particularly useful compositions can be obtained by using a mixture of two or more kinds of the present compounds, or by the use of synergists, such as those known for use with the general class of "pyrethroid" compounds, especially α-[2-(2-butoxyethoxy)ethoxy]-4,5-methylenedioxy-2-propyltoluene also known as piperonyl butoxide, 1,2-methylenedioxy-4-[2-(octylsulfinyl)propyl]benzene, 4-(3,4-methylenedioxyphenyl)-5-methyl-1,3-dioxane also known as safroxane, N-(2-ethyhexyl)bicyclo-[2,2,1]hept-5-ene-2,3-dicarboximide, octachlorodipropyl ether, isobornyl thiocyanoacetate, and other synergists used for allethrin and pyrethrin. Useful compositions can be prepared with other biological chemicals including other cyclopropanecarboxylates, organic phosphate type insecticides and carbamate type insecticides.

The compositions of the invention are applied in sufficient amount to supply the effective dosage of active ingredient at the locus to be protected. This dosage is dependent upon many factors, including the carrier employed, the method and conditions of application, whether the formulation is present at the locus in the form of an aerosol, or as a film, or as discrete particles, the thickness of film or size of particles, the insect or acarine species to be controlled and the like, proper consideration and resolution of these factors to provide the necessary dosage of active material at the locus being within the skill of those versed in the art. In general, however, the effective dosage of active ingredient of this invention at the locus to be protected—i.e., the applied dosage—is of the order or 0.01% to 0.5% based on the total weight of the formulation, though under some circumstances the effective concentration will be as little as 0.001% or as much as 2%, on the same basis.

ILLUSTRATIVE EMBODIMENTS

The invention is illustrated by the following embodiments which describe the preparation of typical species of the invention. The embodiments are presented for the purpose of illustration only and should not be regarded as limiting the invention in any way. The identity of the products, including intermediates, was confirmed by elemental, infrared and nuclear magnetic resonance spectral (NMR) analyses as necessary.

EMBODIMENT 1

(1R,cis)-1-(2,2-Dimethoxyethyl)-2,2-dimethyl-3-(2-oxopropyl)cyclopropane

Ozone was passed through 81.6 g of (+)-$\Delta^3$-carene in 140 ml of methanol at −70° C. at a rate of 3 1/min for about 6 hours until appearance of a blue color indicated an excess of ozone was present in the reaction mixture. The reaction mixture was purged with air to remove excess ozone and 60 ml of methyl sulfide was added. The resulting mixture was stirred and slowly warmed to room temperature overnight, at which time the reaction mixture gave a negative test to starch-iodide paper. The methanol was stripped off and the product was diluted with 1 liter of ether, washed three times with 300 ml of water and then with 300 ml of a saturated sodium chloride solution. The resulting ether phase was dried with magnesium sulfate, filtered and stripped to give 112.5 g of product as an oil, bp 98°–100° C. at 1 mm.

EMBODIMENT 2

((1R,cis)-(2-(2,2-Dimethoxyethyl)-3,3-dimethylcyclopropyl))methyl acetate

To a stirred solution of the product from Embodiment 1 above in 1 liter of methylene chloride at 20° C., was added 140 g of 70% m-chloroperbenzoic acid at 20°–30° C. over a period of 2 hours. The mixture was stirred at room temperature for an additional 18 hours, after which the excess peroxy acid was decomposed with 10% sodium sulfite solution. The solid products products were filtered and washed with methylene chloride. The methylene chloride phase was washed twice with 30 ml of saturated sodium bicarbonate solution and then with saturated sodium chloride solution. The methylene chloride phase was then dried with magnesium sulfate, filtered and stripped to give 125 g of an oil containing a small amount of solid material. This product was diluted with pentane and cooled in ice water. The resulting solid material was filtered and the remaining solution was stripped with an aspirator and pump to give 112.3 g of product as an oil, bp 98°100° C. at 1 mm.

EMBODIMENT 3

((1S,cis)-2,2-Dimethyl-3-(2,2-dimethoxyethyl)cyclopropyl)methanol

A solution of 100 g of the product from Embodiment 2 above, 32 g of 85% potassium hydroxide, 15 ml of water and 600 ml of methanol was stirred at room temperature for about 18 hours. Methanol was then stripped and the remaining reaction mixture was diluted with water. The resulting aqueous solution was extracted twice with chloroform. The combined chloroform phases were washed with water and then with saturated sodium chloride solution. The chloroform phase was dried with magnesium sulfate, filtered and stripped to give 85 g of a yellow oil. This oil was distilled to give 63 g of product, bp 73°–75° C. at 0.05 mm.

EMBODIMENT 4

(1R,cis)-3-(Ethoxymethyl)-2,2-dimethyl-1-(2,2-dimethoxyethyl) cyclopropane

To a stirred mixture of sodium hydride, from 5.8 g of 50% dispersion of sodium hydride in mineral oil washed with pentane, and 200 ml of dry dimethylformamide was added dropwise, at room temperature, 22.6 g of the product from Embodiment 3 above; mild gas evolution took place. Subsequently, 37.4 g of ethyl iodide was added dropwise at 10°–25° C. over a period of ½ hour during which time vigorous gas evolution was observed. After stirring for about 18 hours at room temperature, an additional 6 g of sodium hydride in 100 ml of dimethylformamide was added and the reaction mixture was stirred at room temperature for 3 days. The mixture was quenched with water after decomposing any excess sodium hydride with ethanol. The aqueous solution was extracted with ether and the ether phase was washed with water. The ether phase was then dried with magnesium sulfate and stripped to give 30 g of an oil. This oil was distilled to give 20.3 g of desired product, bp 69°–70° C. at 0.2 mm.

EMBODIMENTS 5–7

Using procedures similar to those of Embodiment 4 above, the following cyclopropane derivatives were prepared: 3-methoxymethyl-2,2-dimethyl-1-(2,2-dimethoxyethyl)cyclopropane, bp 60° C. at 0.3 mm Hg; 3-propoxymethyl-2,2-dimethoxyethyl)cyclopropane, bp 75°–77° C. at 0.2 mm Hg; and 3-benzyloxymethyl-1-(2,2-dimethoxyethyl)cyclopropane, bp 125°–130° C. at 0.2 mm Hg.

EMBODIMENT 8

(1R,cis)-2,2-Dimethyl-3-(ethoxymethyl)cyclopropaneacetaldehyde

A 30 g solution of the acetal from Embodiment 4 above in 500 ml of a 2:1 mixture of acetic acid and water was stirred at room temperature for about 6 hours. The reaction mixture was poured into 1 liter of water. The aqueous mixture was extracted with methylene chloride, and the methylene chloride phase was washed with water, then with a saturated sodium bicarbonate solution and finally with a saturated sodium chloride solution. The methylene chloride phase was dried with magnesium sulfate and stripped to give 28 g of an oil. The oil was distilled to give 21.6 g of product, bp 64°–66° C. at 0.5 mm and $[\alpha]_D^{25}+25.6°(CHCl_3)$; c=0.02 g/cc.

EMBODIMENTS 9–11

Using procedures similar to those of Embodiment 8 above, the following cyclopropane derivatives were prepared: 2,2-dimethyl-3-(methoxymethyl)cyclopropaneacetaldehyde, bp 55°–57° C. at 0.3 mm Hg; 2,2-dimethyl-3-(propoxymethyl)cyclopropaneacetaldehyde, bp 75°–78° C. at 1 mm Hg; and 2,2-dimethyl-3-(benzyloxymethyl)cyclopropaneacetaldehyde, bp 115°–124° C. at 0.15–0.25 mm Hg.

EMBODIMENT 12

((1R,cis)-2,2-Dimethyl-3-(ethoxymethyl)cyclopropyl)-vinyl acetate

A solution of 20.5 g of the aldehyde from Embodiment 8 above, 60 ml of acetic anhydride and 12.8 g of triethylamine was stirred at room temperature for 10 hours. The reaction mixture was diluted with ether, washed with ice water, ice cold 1N hydrochloric acid, ice cold solution of sodium bicarbonate, and finally with saturated sodium chloride solution. The ether phase was dried with magnesium sulfate, and stripped to give 52 g of an oil. After removal of acetic anhydride at 40° C. and 10 mm Hg, the oil was distilled to give 15.2 g of product, bp 78°–80° C. at 0.3 mm Hg and $[\alpha]_D^{25}-36.2(CHCl_3)$; c=0.02 g/cc.

EMBODIMENTS 13–15

Using procedures similar to those of Embodiment 12 above, the following cyclopropane derivatives were prepared: 2,2-dimethyl-3-(methoxymethyl)cyclopropyl vinyl acetate, bp 75°–77° C. at 0.5 mm Hg; 2,2-dimethyl-3-(propoxymethyl)cyclopropyl)vinyl acetate, bp 85°–88° C. at 0.2 mm Hg; and 2,2-dimethyl-3-(benzyloxymethyl)cyclopropyl)vinyl acetate, bp 121°–127° C. at 0.03 mm Hg.

EMBODIMENT 16

(1R,cis)-2,2-Dimethyl-3-(ethoxymethyl)cyclopropanecarboxaldehyde

Ozone was passed through a stirred solution of 14.5 g of the acetate from Embodiment 12 above in 120 ml of methylene chloride at −70° C. at a rate of 1 liter/min for 2 hours until the appearance of a blue color indicated the presence of excess ozone. The reaction mixture was purged with air to remove excess ozone and the methylene chloride stripped below 20° C. The resulting product was diluted with 200 ml of ether containing 50 ml glacial acetic acid. The solution was treated at 15°–25° C. with 25 g of zinc dust added portionwise over 1 hour. This reaction mixture was stirred for 1hr at 25° C., filtered to remove salts and the solids were washed with ether. The combined ether filtrates were washed with water, saturated sodium bicarbonate solution and finally with saturated sodium chloride solution, dried with magnesium sulfate, and stripped to give 11 g of an oil. This oil was distilled to give 8.4 g of product, bp 63°–66° C. at 1.5 mm Hg and $[\alpha]_D^{25}-46.7°(CHCl_3)$; c=0.02 g/cc.

EMBODIMENTS 17–19

Using procedures similar to those of Embodiment 16 above, the following cyclopropane compounds were prepared: 2,2-dimethyl-3-(methoxymethyl)cyclopropanecarboxaldehyde, bp 55°–58° C. at 1.5 mm Hg; 2,2-dimethyl-3-(propoxymethyl)cyclopropanecarboxaldehyde, bp 65°–67° C. at 0.5 mm Hg; and 2,2-dimethyl-3-(benzyloxymethyl)cyclopropanecarboxaldehyde, bp 120°–123° C. at 0.3 mm Hg.

EMBODIMENT 20

(1R,cis)-2,2-Dimethyl-3-(2,2-ethoxymethyl)cyclopropanecarboxylic acid

To a stirred solution containing 7.7 g of the aldehyde from Embodiment 16 above in 100 ml of acetone and 20 ml of water was added portionwise, over ½ hour, 6 g of potassium permanganate while maintaining the temperature at 5°–10° C. The resulting reaction mixture was allowed to warm to room temperature while stirring for 4 hours. The mixture was filtered, and the filtrate was decolorized with a 10% sodium bisulfite, and, after filtration adjusted to a pH of 4 by addition of concentrated hydrochloric acid. The solution was extracted with methylene chloride and the extract was washed with water, and dried with magnesium sulfate. The solvent was stripped to give 6.4 g of a thick oily liquid. Crystallization from hexane gave 4.9 g of product as a colorless solid; mp 40°–40.5° C.

EMBODIMENTS 21–23

Using procedures similar to Embodiment 20 above, the following (1R,cis)-2,2-dimethyl-3-(hydrocarbyloxymethyl)cyclopropanecarboxylic acids were prepared: 2,2-dimethyl-3-(methoxymethyl)cyclopropanecarboxylic acid, mp 42°–43° C.; 2,2-dimethyl-3-(propoxymethyl)cyclopropanecarboxylic acid, bp 100° C. at 0.05 mm Hg; and 2,2-dimethyl-3-(benzyloxymethyl)cyclopropanecarboxylic acid, bp 110°–120° C. at 0.05 mm Hg.

EMBODIMENT 24

((1S,cis)-(2,2-dimethyl-3-(2-oxoethyl)cyclopropyl)-)methyl acetate 112 g of the product of Embodiment 2 above was treated with 1670 ml of a 2:1 solution of acetic acid: water at room temperature for 15 hours. The reaction mixture was poured into 2 liters of water and extracted twice with 1 liter of methylene chloride. The methylene chloride phase was washed with 2 liters of water and then with 500 ml of saturated sodium bicarbonate solution. The resulting methylene chloride phase was dried with magnesium sulfate and stripped to give 85 g of product as an oil, bp 75°-77° C. at 0.4 mm.

EMBODIMENT 25

((1R,cis)-2-(3-acetoxymethyl-2,2-dimethylcyclopropyl))vinyl acetate 85 g of the product from Embodiment 24 above was treated while stirring with 99 g of triethylamine and 230 ml of acetic anhydride at room temperature for about 18 hours. The reaction mixture was diluted with ether. The resulting solution was washed with ice water, then with ice cold sodium bicarbonate solution and finally with saturated sodium chloride solution. The ether phase was dried with magnesium sulfate and stripped to give 350 g of an oil. This oil was distilled to remove acetic anhydride at 40° C. and 10 mm Hg and the resulting residue was distilled to give 80 g of product; bp 93°-96° C. at 0.1 mm Hg.

EMBODIMENT 26

(1R,cis)-3-(acetoxymethyl)-2,2-dimethylcyclopropanecarboxaldehyde

Ozone was passed through 25 g of the product from Embodiment 25 above in 150 ml methylene chloride at a rate of 3 1/min until appearance of a blue color indicated an excess of ozone was present in the reaction mixture. Ozone treatment was continued at a rate of 1 1/min for an additional 40 minutes. The reaction mixture was purged with air to remove excess ozone and stripped below 25° to a clear pale yellow oil. This oil was dissolved in 250 ml acetic acid and 40 g of zinc dust was added portionwise over a 2 hour period at 10°-20° C. The resulting mixture was stirred 2 additional hours and then filtered through celite. The filtrate was washed with water, then with saturated sodium bicarbonate solution and finally with a saturated sodium chloride solution. The resulting solution was dried with magnesium sulfate and stripped to give 16.1 g of product as a colorless oil, bp 58°-60° C. at 0.1 mm.

EMBODIMENT 27

(1R,cis)-2,2-Dimethyl-3-(acetoxymethyl)cyclopropanecarboxylic acid

To a solution of 21.0 g of the product of Embodiment 26 above, 250 ml of acetone and 50 ml of water at 5° C., was added 14.8 g of potassium permaganate portionwise over 40 minutes at 5°-10° C. The reaction mixture was then warmed to room temperature while stirring for 6 hours. The mixture was filtered and the filtrate was treated with 10% sodium bisulfite solution to destroy excess permanganate and, after filtration, stripped to remove acetone and adjusted to a pH of 4 with concentrated hydrochloric acid. The resulting solution was extracted three times with 100 ml methylene chloride. The combined methylene chloride extracts were washed with water, then with saturated sodium chloride solution, dried with magnesium sulfate and stripped to give 19 g of a thick oil which crystallized upon cooling overnight. This product was triturated with cold pentane and filtered to give 13.7 g of product as a solid; mp 78°-79° C.

EMBODIMENT 28

α-Cyano-3-phenoxybenzyl (1R,cis)-2,2-dimethyl-3-(acetoxymethyl)cyclopropanecarboxylate A mixture of 1.1 g of the product from Embodiment 27 above, 0.6 g of triethylamine, 1.7 g of α-cyano-3-phenoxybenzyl bromide in 10 ml of ethyl acetate was refluxed for 1.5 hours to form a white precipitate. The reaction mixture was cooled, washed with water and dried with magnesium sulfate. The resulting mixture was chromatographed on silica gel using 5:1 pentane-ether as eluent to give 1.3 g of product as a viscous pale yellow oil; $[\alpha]_D^{25}$4.2°(CHCl$_3$); c=0.024 g/cc.

EMBODIMENT 29

α-Cyano-3-phenoxybenzyl (1R,cis)-2,2-dimethyl-3-(ethoxymethyl)cyclopropanecarboxylate A mixture of 1.7 g of 2,2-dimethyl-3-ethoxymethylcyclopropanecarboxylic acid (as prepared in Embodiment 20), 2.9 g of α-cyano-3-phenoxybenzyl bromide and 1 g of triethylamine in 25 ml of ethyl acetate was refluxed for 3 hours. The reaction mixture was left standing at room temperature overnight. The mixture was diluted with ether, washed with water and then with saturated sodium chloride solution. The ether phase was dried with magnesium sulfate and stripped to give 3.6 g of a thick oil. This oil was chromatographed on silica gel using a 5:1 pentane-ether solution as eluent to give 2.8 g of the desired product as a thick yellow oil; $[\alpha]_D^{25}$+23.8°(CHCl$_3$); c=0.02 g/cc.

EMBODIMENT 30-33

Using procedures similar to those described in Embodiment 29 above, the following cyclopropanecarboxylates were prepared: α-cyano-3-phenoxybenzyl (1R,cis)-2,2-dimethyl-3-(methoxymethyl)cyclopropanecarboxylate, 3-phenoxybenzyl (1R,cis)-2,2-dimethyl-3-(ethoxymethyl)cyclopropanecarboxylate, α-cyano-3-phenoxybenzyl (1R,cis)-2,2-dimethyl-3-(propoxymethyl)cyclopropanecarboxylate and α-cyano-3-phenoxybenzyl (1R,cis)-2,2-dimethyl-3-(benzyloxymethyl)cyclopropanecarboxylate.

I claim:

1. A compound of the formula

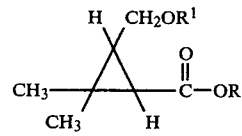

wherein $R^1$ is an alkyl group containing from 1 to 3 carbon atoms, a benzyl group or an acetyl group and R is 3-phenoxybenzyl or α-cyano-3-phenoxybenzyl with the proviso that when R is α-cyano-3-phenoxybenzyl then alcohol moiety is in the R,S-racemic or the S-optical configuration.

2. A compound according to claim 1 wherein R is α-cyano-3-phenoxybenzyl.

3. A compound according to claim 2 wherein $R^1$ is ethyl.

4. A compound according to claim 2 wherein $R^1$ is acetyl.

5. A compound according to claim 2 wherein $R^1$ is n-propyl.

6. A compound according to claim 1 in the (1R,cis) form.

7. A pest control composition comprises a pest controlling effective amount of compound according to claim 1 and at least one agriculturally acceptable surface active agent or carrier therefore.

8. A method of controlling pests which comprises applying to the pests or their habitat a pest controlling effective amount of a compound according to claim 1.

* * * * *